(12) United States Patent
West et al.

(10) Patent No.: US 9,103,809 B2
(45) Date of Patent: Aug. 11, 2015

(54) LIQUID HANDLER WITH DUAL PIPETTING GROUPS

(75) Inventors: Daniel West, Campbell, CA (US); David Knorr, San Leandro, CA (US); James E. Young, La Honda, CA (US); Kimberly Subrahmanyan, Los Altos, CA (US); Nicholas Fleming, San Francisco, CA (US); Randy K. Roushall, Redwood City, CA (US)

(73) Assignee: Agilent Technologies, Inc., Loveland, CO (US)

( * ) Notice: Subject to any disclaimer, the term of this patent is extended or adjusted under 35 U.S.C. 154(b) by 471 days.

(21) Appl. No.: 13/453,867

(22) Filed: Apr. 23, 2012

(65) Prior Publication Data
US 2013/0280145 A1    Oct. 24, 2013

(51) Int. Cl.
*B01L 3/02* (2006.01)
*G01N 35/10* (2006.01)
*G01F 11/00* (2006.01)

(52) U.S. Cl.
CPC ............... *G01N 35/1065* (2013.01); *B01L 3/02* (2013.01); *B01L 2200/0605* (2013.01); *B01L 2200/0642* (2013.01); *G01F 11/006* (2013.01); *G01N 2035/1076* (2013.01); *Y10T 29/49826* (2015.01)

(58) Field of Classification Search
CPC .............. B01L 3/02; B01L 2200/0605; B01L 2200/0642; G01F 11/006
USPC ........................................ 422/509; 73/864.25
See application file for complete search history.

(56) References Cited

U.S. PATENT DOCUMENTS

| | | | |
|---|---|---|---|
| 7,025,933 B2 * | 4/2006 | Ganz et al. | 422/63 |
| 2003/0213313 A1 * | 11/2003 | Katagi | 73/864.25 |
| 2007/0264725 A1 | 11/2007 | Wiggli et al. | |

* cited by examiner

*Primary Examiner* — Jan Ludlow

(57) ABSTRACT

An automated liquid handling system is disclosed. A system includes a first pipetting group, which includes at least one pipettor, movably arranged on a first arm; and a second pipetting group, which includes at least one pipettor, movably arranged on a second arm, wherein the first arm and the second arm are movably arranged on at least one track such that the first arm and the second arm can independently move along the at least one track while keeping the first arm parallel with the second arm, wherein the at least one pipettor of the first pipetting group is arranged on a side of the first arm facing the second pipetting group, wherein the at least one pipettor of the second pipetting group is arranged on a side of the second arm facing the first pipetting group.

14 Claims, 15 Drawing Sheets

LIQUID HANDLER WITH DUAL PIPETTING GROUPS

FIELD OF THE INVENTION

This invention relates generally to liquid handling systems, particularly to automatic liquid handling systems capable of high throughputs.

BACKGROUND

Many life science and diagnostic assays often involve parallel processing of a large number of samples. Liquid handling is an important part of most assays. The development of automated liquid handling systems has brought improved efficiency and safety to laboratory workflow.

Efficiency is mostly achieved by the use of automated robotic workstations. Various workstations are available from vendors, such as the BRAVO™ workstation from Agilent Technologies, Inc. (Santa Clara, Calif.). The main parts of such robotic workstations include automatic liquid handling systems. An automated liquid handling system can provide high throughput and automated processing of liquid samples.

An automated liquid handling system typically includes one or more pipettors arranged as an assembly that can transfer a liquid sample from a source to the desired locations in the work area. For example, FIG. 1 shows a schematic of a liquid handling system (pipetting instrument) 100, which includes a single gantry 101 that controls the movements of pipettor 102. The pipettor 102 can typically move in the X, Y, and Z axis directions. To enable these movements, the pipettor 102 is arranged on a track (not shown) that allows the pipettor 102 to move in the Y axis direction (the direction in-and-out of the plane of the drawing), and the gantry 101 is arranged on a track 105 such that the gantry can move in the X-axis direction (left and right in this view). After moving to the desired plate 103 on the work platform in the pipetting instrument 100, the pipettor 102 can move in the Z-axis direction (up-and-down direction in this view) to aspirate or deliver a liquid sample.

The single pipetting group (single gantry) liquid handling system as illustrated in FIG. 1 (or a variation of this configuration) is used in current commercial liquid handling system, such as Biomek™ FX from Beckman-Coulter, Inc. (Brea, Calif.), Freedom EVO™ from Tecan Group, Ltd. (Switzerland), and STAR Line™ from Hamilton Company (Reno, Nev.).

A new system with two blocks on an arm of a robot manipulator is disclosed in U.S. Patent Application Publication No. 2007/0264725. Each block contains two or more pipettes with rigid spacings between them to accommodate well spacings of the existing microtiter plates. The two blocks may be interleaved or interlaced, thereby halving the spacings between the pippetes.

While these prior art liquid handling systems have proven useful, there remains a need for more flexible liquid handling systems.

BRIEF DESCRIPTION OF THE DRAWINGS

The accompanying drawings illustrate several embodiments of the invention and, together with the description, serve to explain the principles of the invention.

DETAILED DESCRIPTION OF THE INVENTION

Figure 1:
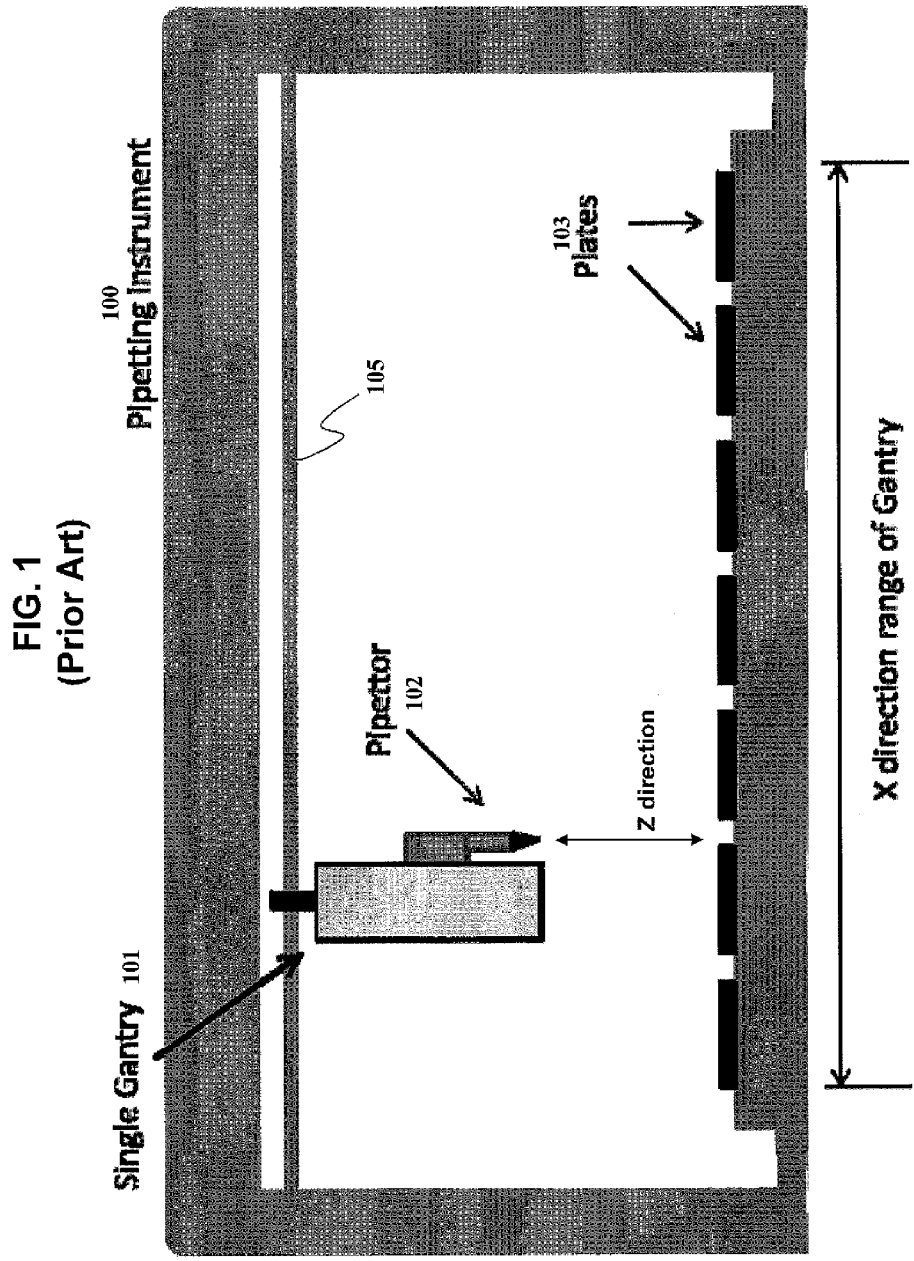
FIG. 1 shows a schematic of a conventional pipetting instrument having a single gantry.

Embodiments of the present invention relate to automated liquid handling systems having two or more banks of pipettors, wherein each of the pipettors can move independently. Each bank of pipettors is arranged on one gantry. Thus, embodiments of the invention relate to systems with two or more gantries. By having two or more pipetting groups, a liquid handling system of the invention can have higher throughputs and are more flexible, allowing such a system to perform tasks that would not be possible (or would be cumbersome and difficult to do) with a single pipetting group or with a two-gentry system that does not allow independent movements of individual pipettors.

While embodiments of the invention may include two or more gantries, the following discussion may use a dual-gantry system for illustration. One skilled in the art would appreciate that the use of a dual-gantry system is for clarity of illustration, and is not intended to limit the scope of the invention. In addition, for clarity of description, the directions of movements may be referred to as the X, Y, and Z-axis directions, which correspond to the left-and-right, back-and-forth, and up-and-down directions, respectively, when a user faces the front of a workstation.

The term "gantry" as used herein refers to an assembly that includes a Y-spanning frame (which may be referred to as "an arm") that includes one or more tracks (or rails) on which pipettors can move in the Y-axis direction. In a broader sense, the "gantry" is also used to refer to the assembly including the pipettors attached thereto.

The term "pipettor" refers to a device for metering or transferring a liquid. A pipettor typically includes a barrel and a tip adaptor portion that is configured to accept a tip (which is typically replaceable or disposable). As used herein a "pipettor" may also include the mechanism or parts that allow it to couple to the Z-axis or Y-axis movement mechanism. A pipettor may be fit into an adaptor card before being assembled on a Y-spanning frame. Such an adaptor card may be referred to as a "pipettor card." A pipettor card may include a circuit board for the control and sensing of the movement and/or a moving mechanism (a motor, a nut for a screw drive, etc.).

As used herein, the term "a pipetting group" refers to the pipettors on the same gantry. A pipetting group may include a single pipettor or multiple pipettors (e.g., 2, 3, 4, 5, 6, 7, 8, or more pipettors).

The term "spacing" refers to a distance between two neighboring objects (e.g., two pipettors or two wells on a microtiter plate) measured from the centers of the neighboring objects. For example, a spacing between the two neighboring pipettors may refer to the distance measured from the tip of one pipettor to the tip of the next pipettor. Similarly, a spacing between two wells in a plate may refer to the distance between the center of the two neighboring wells.

The term "independent movement" or "independently move" refers to the ability of a pipettor to move in the Y-axis or Z-axis direction without coordinating with other pipettors or the ability of a gantry to move in the X-axis direction without coordinating with other gantries.

Figure 2:
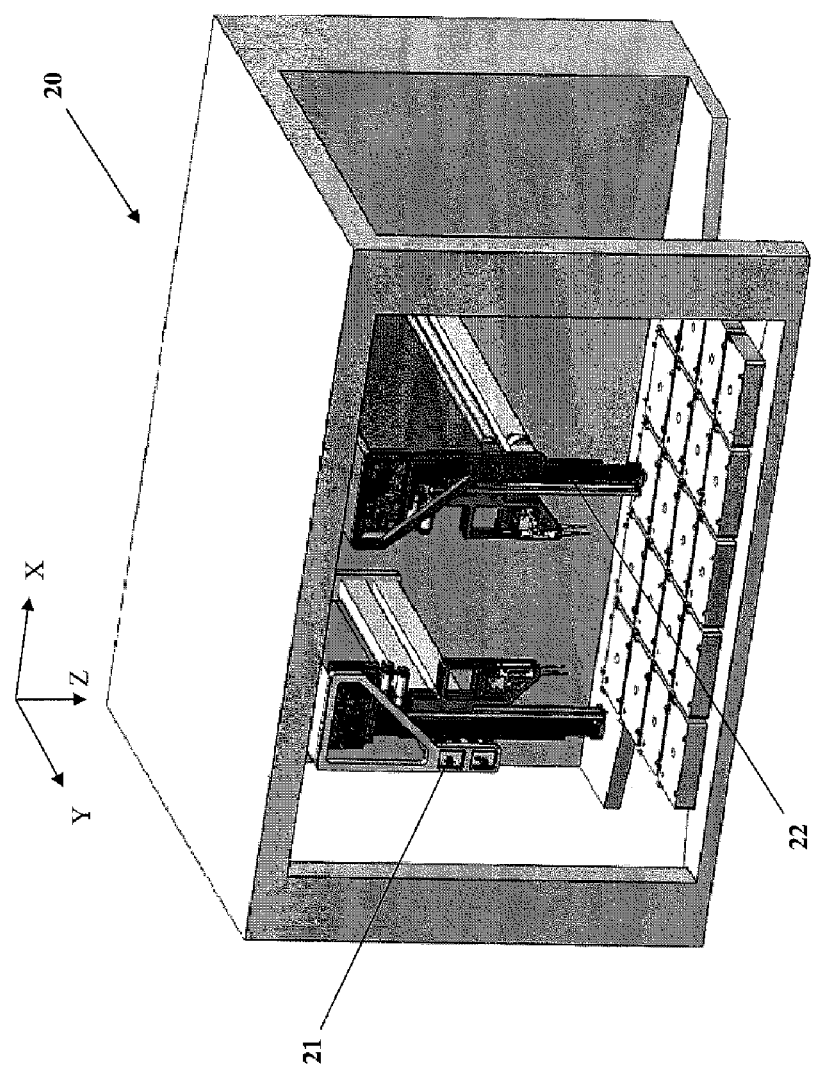
FIG. 2 shows a schematic of a pipetting instrument having dual gantries in accordance with one embodiment of the invention.

As an example, FIG. 2 shows a schematic illustrating a dual-gantry liquid handling system in accordance with embodiments of the invention. As shown, a system 20 includes two pipetting groups (or pipetting banks) 21 and 22. Each pipetting group includes one or more pipettors and X, Y, and Z-axis movement mechanisms. A dual-gantry system of the invention not only provides high throughputs, but also has added capabilities that are not available to a single-gantry system or a prior art dual-gantry system. The various functions that can be performed by each pipetting group 21 or 22 and by a combination of both pipetting groups 21 and 22 will be described later.

Figure 3:
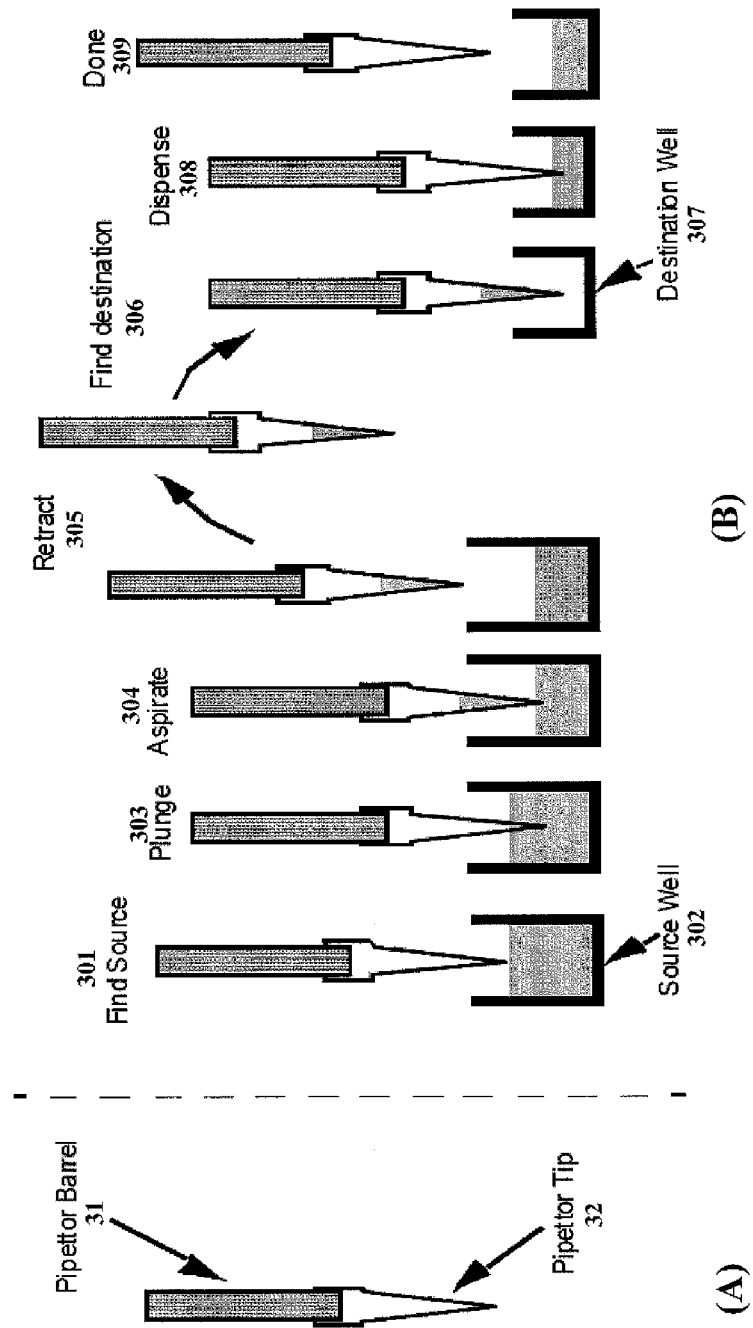
FIG. 3(A) shows a schematic of a conventional pipettor.
FIG. 3(B) shows a schematic illustrating a typical cycle of a pipetting action.

Pipettors typically include four functions; aspirate, dispense, liquid level detect, clot detect. FIG. 3(A) shows a schematic illustration of a pipettor commonly used in liquid handling systems. As shown, a pipettor typically includes a pipettor barrel 31 and a pipettor tip 32. The tips will touch the solutions or samples. To avoid contaminations, the tips may be disposable.

A pipetting gantry having the X, Y and Z axes of motion can position pipettor tips accurately in fluid reservoirs to withdraw a liquid sample, and then retract (in the Z-axis direction) the pipettor. The gantry then moves the pipettor (in the X-axis and Y-axis directions) to the next pipette operating position (e.g., the target tube or well), where the aspired liquid may be dispensed into the target tube or well.

FIG. 3(B) shows a schematic illustrating the various steps involved in a typical pipetting cycle. As shown, one first finds a source (step 301), which for example may be a fluid sample in a source well 302. After finding the source, the pipette is plunged into the source (step 303) and the sample is aspired into the pipette (step 304). Then, the pipette retracts from the source (step 305) and finds the destination (step 306), which for example may be the destination well 307. Once the destination is found, the pipette dispenses the sample (step 308). After dispensing the sample, the pipetting cycle is done (step 309).

As illustrated in FIG. 3(B), a pipettor needs to be able to move up and down, as well as to the correct destination coordinates. In an automated liquid handling system, the X, Y, and Z axis movement mechanisms are provided to accomplish these movements.

The function of the Z-axis movement mechanism is to move a pipetto up and down in a precise and repeatable manner. FIG. 4(A) shows a front view of a gantry 401. One pipettor 402 is visible in this front view. The pipettor 402 comprises a barrel 403 and a tip 404. In accordance with embodiments of the invention, a pipettor 402 may have a dimension that allows it to be packed in a group that would accommodate the dimensions of commonly used labware, such as 96-well plates. For example, the well spacings in a 96-well is about 9 mm. To accommodate this dimension, a liquid handling system of the invention may use pipettors that have a thickness of less than 9 mm to allow close packing of multiple pipettors for use with a 96-well plate. Similarly, to accommodate other types of labware, the dimensions of the pipettors may be accordingly selected to fit the purposes.

The pipettors in a gantry have several features. First, the pipettors can move independent from front to back (the Y-axis direction). In the side view shown in FIG. 4(B), this would be moving left and right. Secondly, the pipettors can move independently up and down. This is called the Z direction. In FIG. 4(B), the pipettors are shown in random Y and Z positions.

In accordance with embodiments of the invention, a Z axis movement mechanism may be provided to a pipettor in any suitable manner. As an example, a pipettor may be housed in a rigid frame (e.g., a pipettor card), which can slide vertically on a track. A track, for example, may comprise two bearings and a linear rail. The rigid frame together with the pipettor may be driven by any suitable moving mechanism to slide on the track. A suitable moving mechanism may comprise, for example, a belt and a gear motor. The motor may include a rotary encoder, or any other suitable encoder, for position controls. One skilled in the art would appreciate that other variations and modifications of the moving mechanisms (e.g., screw drive) are possible without departing from the scope of the invention.

FIG. 4(B) shows a side view of the gantry 401. In this side view 4 pipettors 402, 405, 406, and 407 are visible. The four pipettors are arranged on a Y-spanning frame (or an arm) 408 having in a moveable manner such that they can move along a track 409 on the Y-spanning frame (or an arm) 408. The track 409 run in the front-and-back direction (the Y-axis direction). Thus, track 409 allows the pipettors to move in the Y-axis direction, as illustrated in FIG. 5(A) and FIG. 5(B).

FIG. 5(A) shows a configuration, in which all four pipettors are in the left half of the track, while FIG. 5(B) shows a configuration, in which all four pipettors are packed to the extreme right in this side view. There are many locations in the Y direction that the pipettors can occupy. In general terminology, this independent motion is called "spanning in Y." Furthermore, the pipettor placed in any Y position can have any Z position. In general terminology, this is called "independent Z." The independent movements in the Y and Z directions for each pipettor allow the pipetting gantry system to access source and destination locations independent of each other. This allows for higher throughput of protocols that need complete independent motions, such as a cherry picking protocol.

The movement along the track 409 may be accomplished with any suitable mechanisms, such as a screw drive or a driving belt and motor combination. Again, embodiments of the invention are not particularly limited by the types of movement mechanisms.

Figure 4:
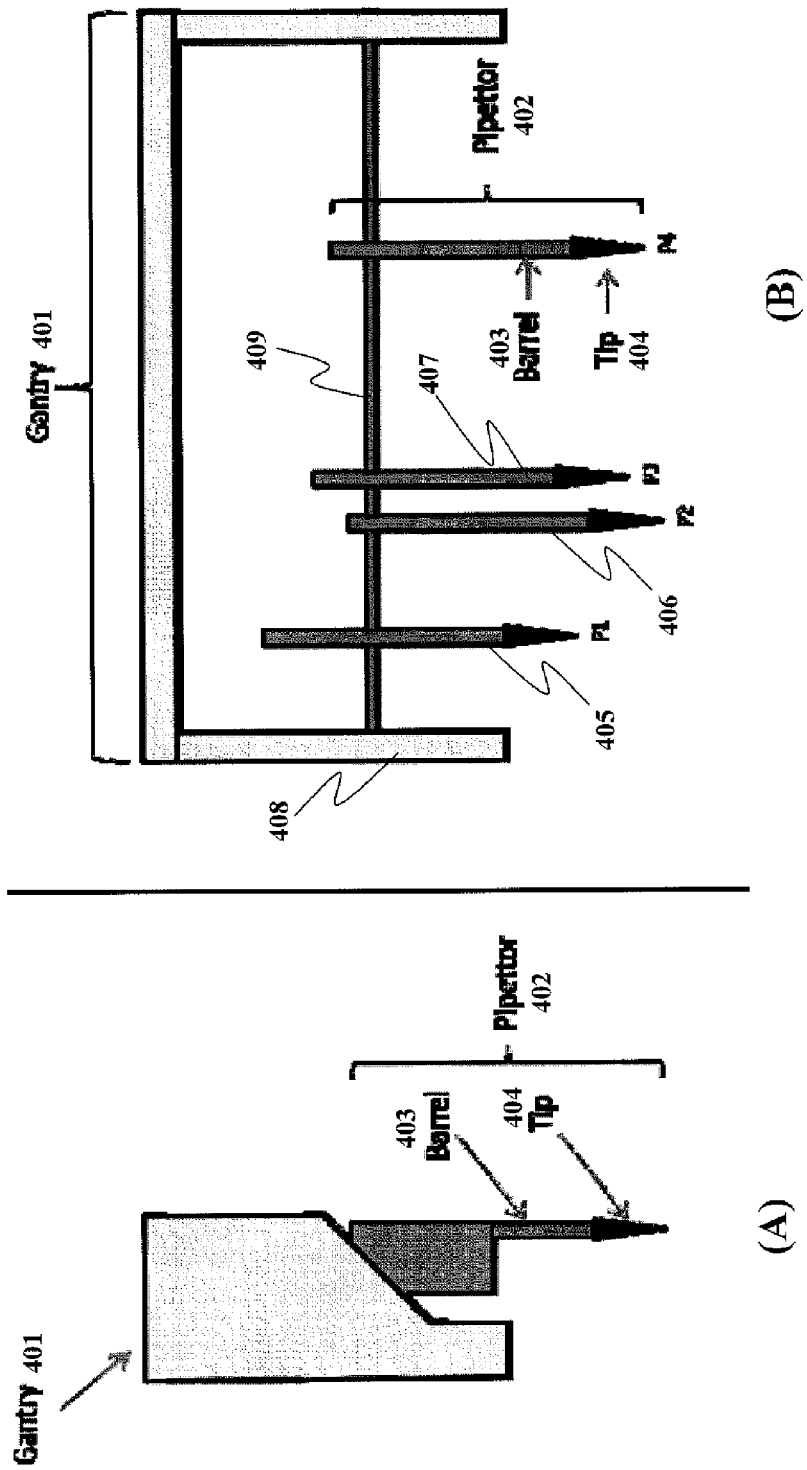
FIG. 4(A) shows a front view of a gantry with a pipettor visible.
FIG. 4(B) shows a side view of a gantry including four pipettors.
Figure 5:
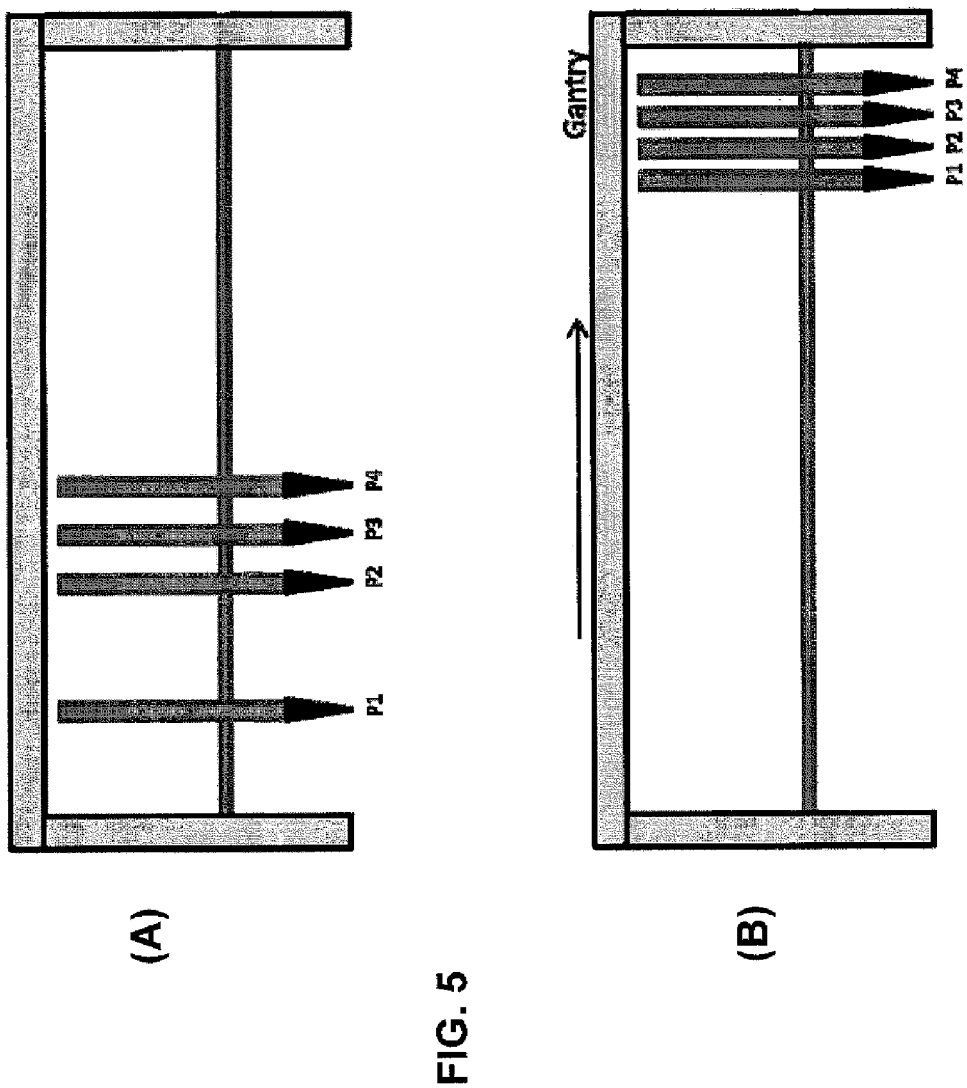
FIG. 5(A) shows a configuration of four pipettors on a gantry.
FIG. 5(B) shows another configuration of four pipettors on a gantry.

While the examples shown in FIGS. 4 and 5 have four pipettors in each gantry. Embodiments of the invention may include any suitable numbers of pipettors on each Y-axis tract in a gantry. For example, the Y axis may contain from four to eight pipettors in preferred embodiments.

Figure 6:
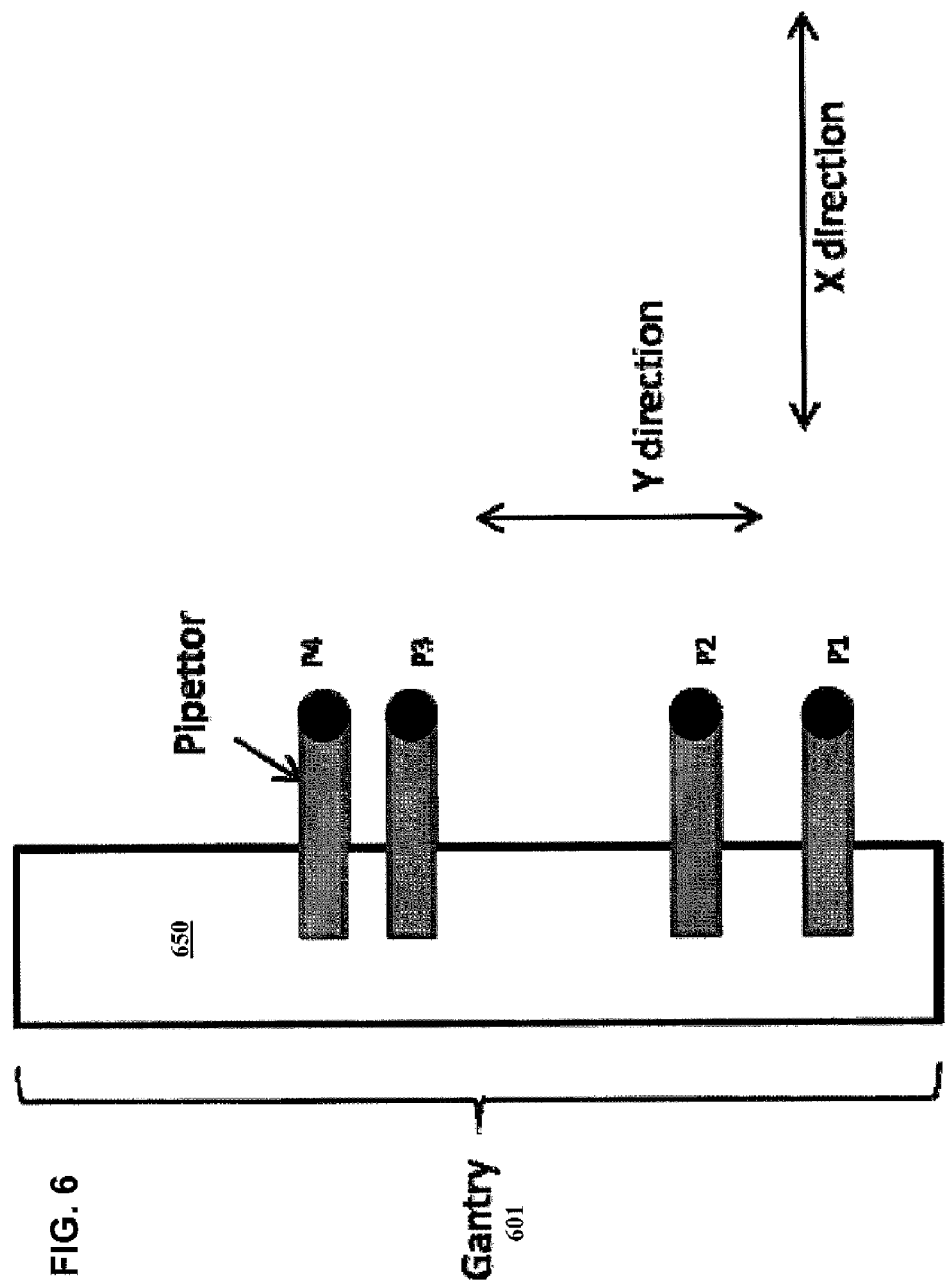
FIG. 6 shows a schematic of a top view of a gantry including four pipettors.

FIG. 6 shows a schematic of a top view of the gantry of FIGS. 4 and 5. In this view, the gantry 601 has four pipettors, P1, P2, P3, and P4, which are arranged to the right of the gantry frame 650. The X and Y directions are as indicated. The pipettors can move along a track (not shown) in the gantry in the Y direction, and the gantry 601 can move in the X direction in the liquid handling system. This combination of movements allows the system to deliver a pipettor to a desired location (X and Y coordinates) in a work area.

As shown in FIG. 6, the pipettors move as a set in the X direction to simplify the design. It is possible to also add independent movement in the X direction. Instruments with pipettors having independent movements in the X direction may be considered as multiple gantries each with only one pipettor.

FIGS. 3-6 illustrate functions of a single gantry having 1 to "many" pipettors with spanning Y and independent Z motions. In such systems, the pipettors are mounted in a single gantry that allows the pipettors to move in the X direction as a common set. For many applications, this configuration works well and is acceptable. The pipettes can easily align themselves with typical labware, such as tubes and microtiter plates, such that the pipettors can access the liquid in the tubes or wells.

For higher throughput protocols, the common practice is to make the motions as quick as possible. This entails good mechanical and controls designs of the gantry system, as well as good software sorting techniques, to quickly move through the list of liquid transfers required to complete the protocol. In addition, customers may be given the ability to add more pipettors for cases that require multiple transfers from the same column (e.g., a common X location). Common pipettor configurations include 4 or 8 pipettors. These configurations are driven by the geometry of microtiter plates, e.g., a 96-well plate, which is organized as 8 rows by 12 columns. With a single gantry system, users can load 8 pipettors and access 1 column of wells in a micro titer plate at a time.

There are a few physical limitations with a single-gantry system. First, the number of pipettors a gantry can hold is somewhat limited. The size of the gantry itself determines how many pipettors can practically be mounted. Secondly, the width of a single pipettor determines how close two pipettors can come together and access common labware. For a 96-well plate, the well to well spacing is 9 mm. Therefore, pipettors have to be narrower than 9 mm if a system is to access adjacent wells at the same time. Lastly, because of a common X location, the pipettors cannot access other columns of plates or non-common X location labware.

Figure 7:
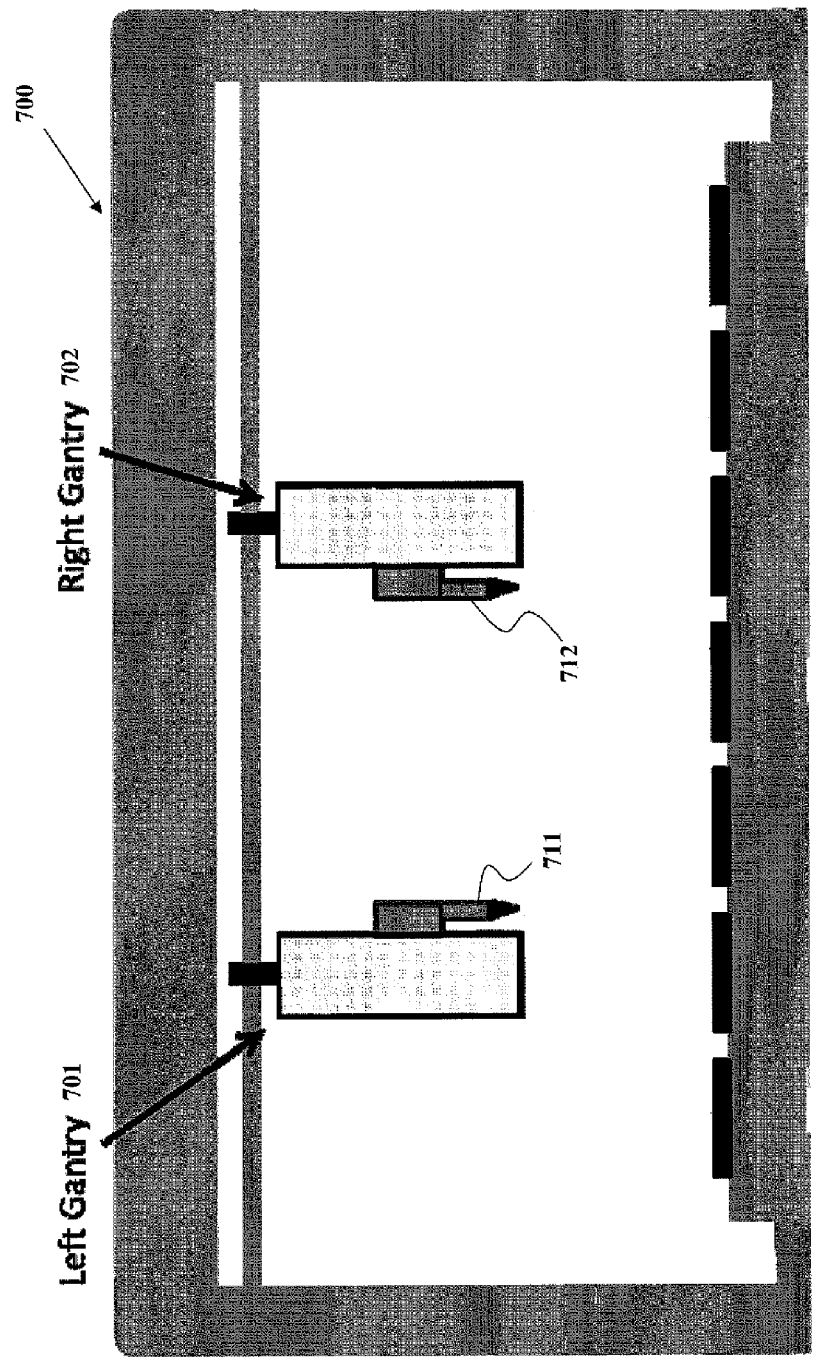
FIG. 7 shows a schematic of dual-gantry liquid handling system in accordance with one embodiment of the invention.

To provide more flexibility and functionalities, embodiments of the invention include more than one gantry—i.e., two or more gantries. For example, FIG. 7 shows a schematic illustrating a dual-gantry automated liquid handling system in accordance with embodiments of the invention. As shown, an automated liquid handling system 700 has two gantries 701 and 702. Each gantry has one or more pipettors. In this view, one pipettor 711 is seen associated with gantry 701, and the other pipettor 712 is seen associated with gantry 702.

As shown in FIG. 7, the gantries have a "X spanning" direction, much like the "Y spanning" concept. Each gantry has its own common X location with an X separation defined as the distance between the tips of the two gantry pipetting sets. With this capability, the system can now pipette on different columns of a single microtiter plate, as well as span across multiple plates up to the entire distance of the pipettable area. That is, one gantry can be at one end of the instrument while the other gantry can be at the other end of the instrument. In general terms, a protocol can double its throughputs by having two independent pipetting systems in one instrument.

Note that the pipettor 711 is arranged to the right of gantry 701, while the pipettor 712 is arranged to the left of gantry 702. Thus, the two sets of pipettors in a dual gantry system are arranged to face each other (i.e., mirror images).

Figure 8:
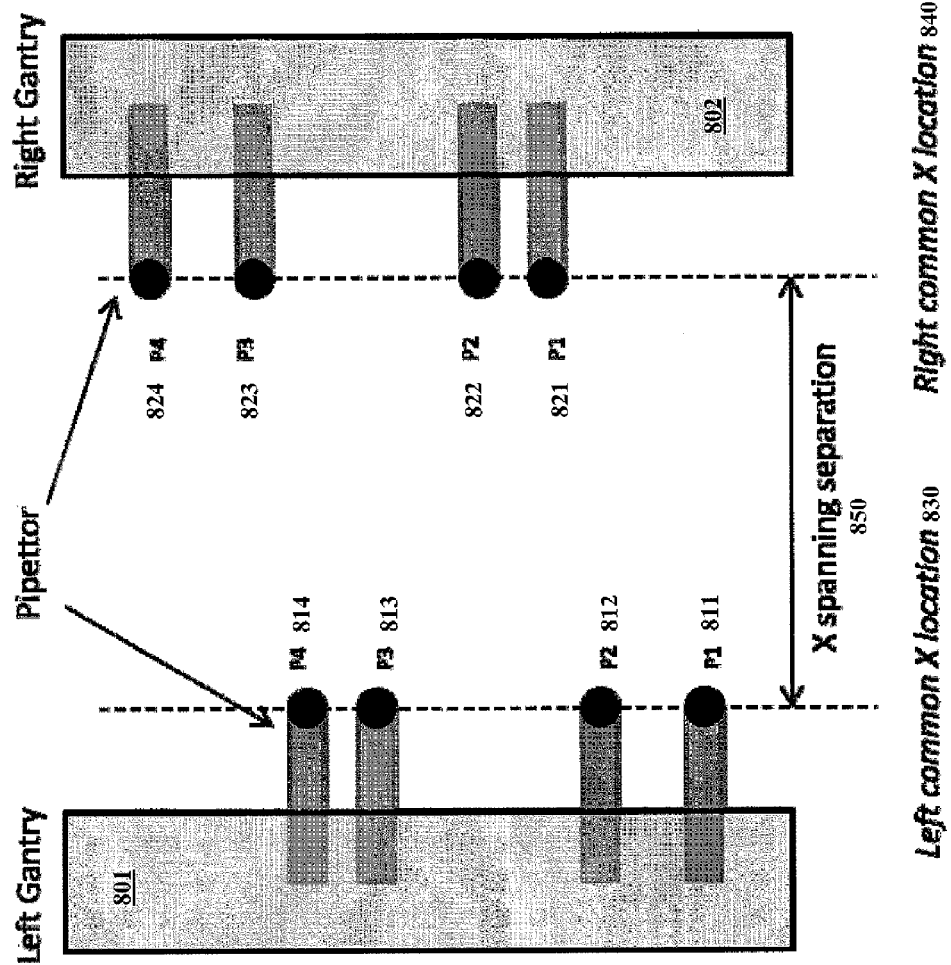
FIG. 8 shows a schematic illustrating a top view of a dual-gantry configuration in accordance with one embodiment of the invention.

The configuration of two banks of pipettors facing each other is more clearly demonstrated in FIG. 8. In FIG. 8, the left gantry 801 has four pipettors 811, 812, 813, and 814, which are aligned at the left common X location 830 and facing to the right. Similarly, the right gantry 802 also has four pipettors 821, 822, 823, and 824, which are aligned at the right common X location 840 and facing to the left. The two banks of pipettors are separated along the X axis by an X spanning separation 850, which will change when either or both gantries move in the X direction.

As shown in FIG. 8, the gantries are mirror images of each other and the "X spanning separation" can be independently changed by each gantry. Each bank of pipettors still maintains the Y and Z direction independence to allow for many more applications of pipetting. This system also has the capability to drive the X spanning separation to a distance of "0," which simply means the two gantries can come together and act as a single gantry system with twice as many pipettors.

Figure 9:
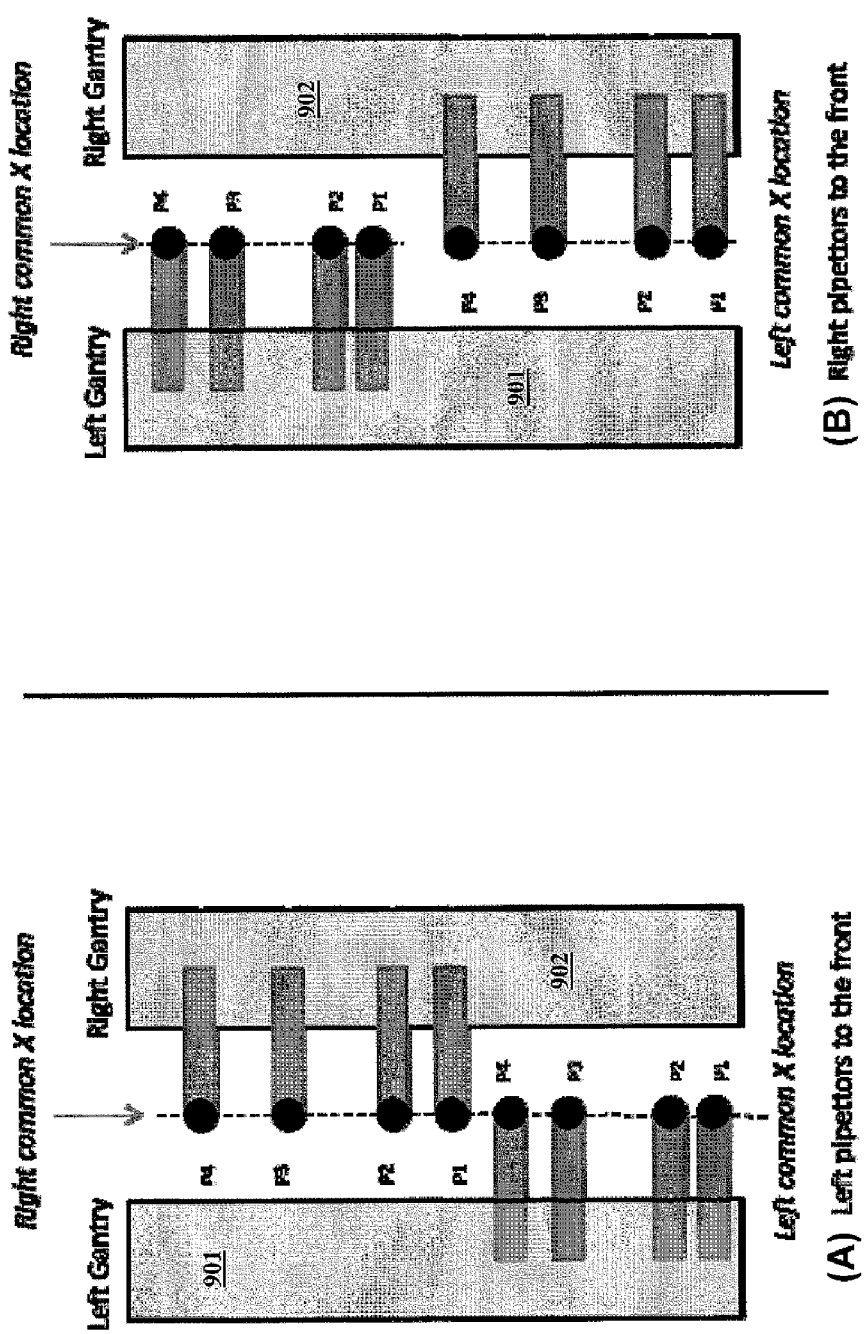
FIG. 9(A) shows a configuration of eight pipettors from two gantries aligned at the same X location in accordance with one embodiment of the invention.
FIG. 9(B) shows another configuration of eight pipettors from two gantries aligned at the same X location in accordance with one embodiment of the invention.

For example, FIG. 9(A) shows a configuration in which the four pipettors on the left gantry 901 are moved to the front, and the four pipettors on the right gantry 902 are moved to the back such that the two sets of pipettors can align at the same X location. In FIG. 9(B), the situation is reversed—i.e., all four pipettors on the left gantry 901 are in the back and all four pipettors on the right gantry 902 are in the front.

Figure 10:
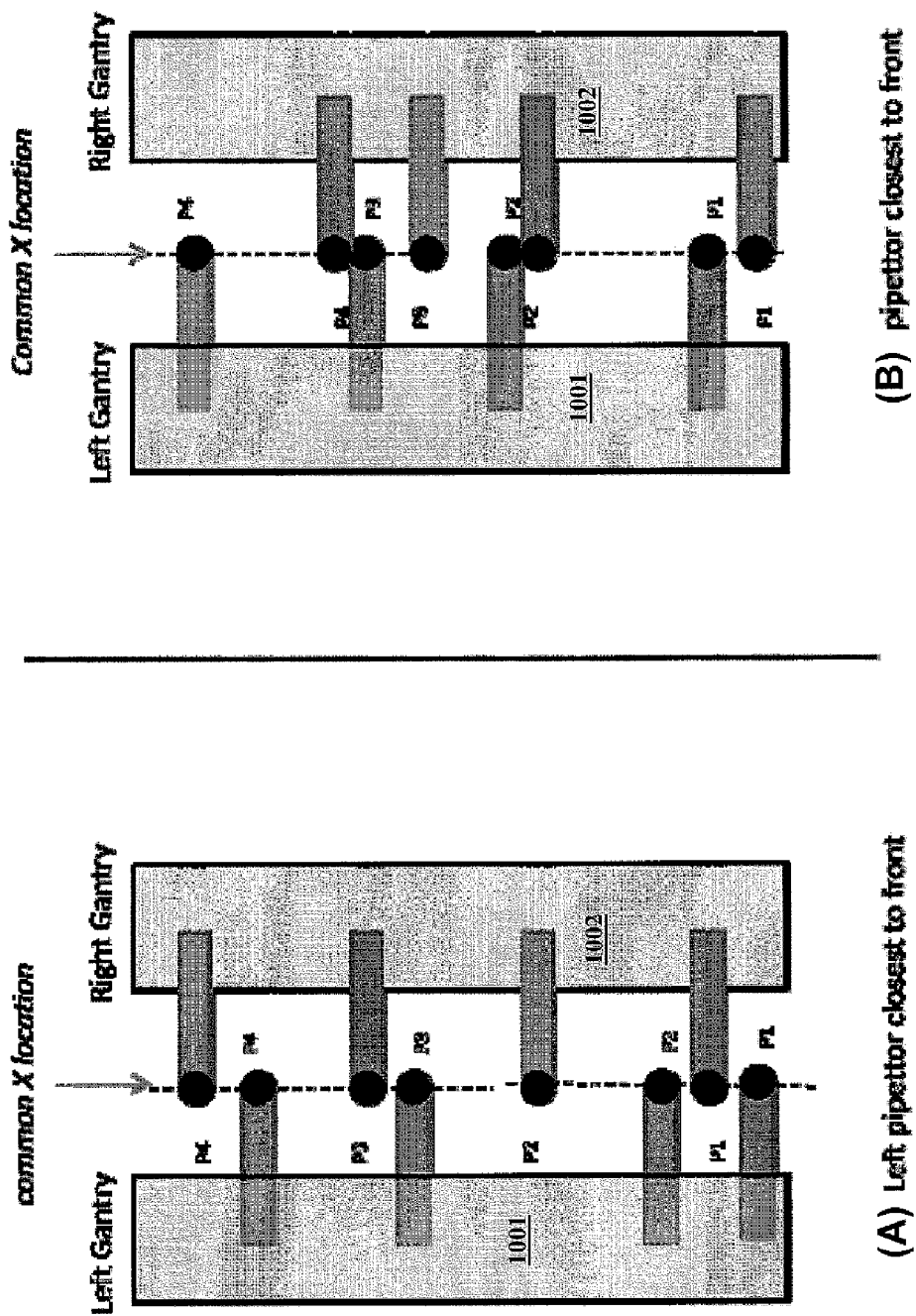
FIG. 10(A) shows another configuration of eight pipettors from two gantries aligned at the same X location in accordance with one embodiment of the invention.
FIG. 10(B) shows another configuration of eight pipettors from two gantries aligned at the same X location in accordance with one embodiment of the invention.

Other configurations are possible to align all pipettors from different gantries at the same X location. For Example, FIG. 10(A) and FIG. 10(B) show two additional configurations, in which a set of pipettors from one gantry interleave with the other set of pipettors from the other gantry. FIG. 10(A) and FIG. 10(B) configurations also illustrate the possibility of having different Y-axis spacings between neighboring pipettors. That is, there can be large spacing between interleaved pipettors or small spacing between interleaved pipettors. The spacing can be adjusted for the applications and not limited by the hardware capability In the configurations shown in FIG. 9(A), FIG. 9(B), FIG. 10(A), and FIG. 10 (B), all pipettors are at the same X location. They may be operated in this configuration—i.e., the two gantries will move in sync in the X direction. In this manner, the system would behave as if the liquid handling system has only one gantry with eight pipettors. In other words, a dual gantry system of the invention can also function as a conventional single-gantry system.

A common approach to achieving pipetting of a single plate or tube rack is to space the pipettors on a grid spacing equivalent to the labware spacing. For example, a 96-well plate has a spacing of 9 mm between wells. If each gantry has only 4 pipettors and the application required simultaneous aspiration or dispensing of a single column at a time to achieve efficient transfer of liquid, then the pipettors from the two gantries could be aligned at the same X location and spaced at 9 mm spacing, as illustrated in FIG. 11(A) and FIG. 11(B).

FIG. 11(A) illustrates one application working with a 96-well plate, in which a dual-gantry system is used as a single-gantry system. In this example, the four pipettors on the left gantry 1101 are arranged in the front and the four pipettors on the right gantry 1102 are arranged in the back. The pipettors are closely packed to provide a 9-mm pitch between the neighboring pipettors in order to fit a standard 96-well plate. While FIG. 11(A) shows one configuration for this operation, FIG. 11(B) shows an alternative, in which the pipettors from the two gantries are interleaved in an alternating fashion.

Figure 11:
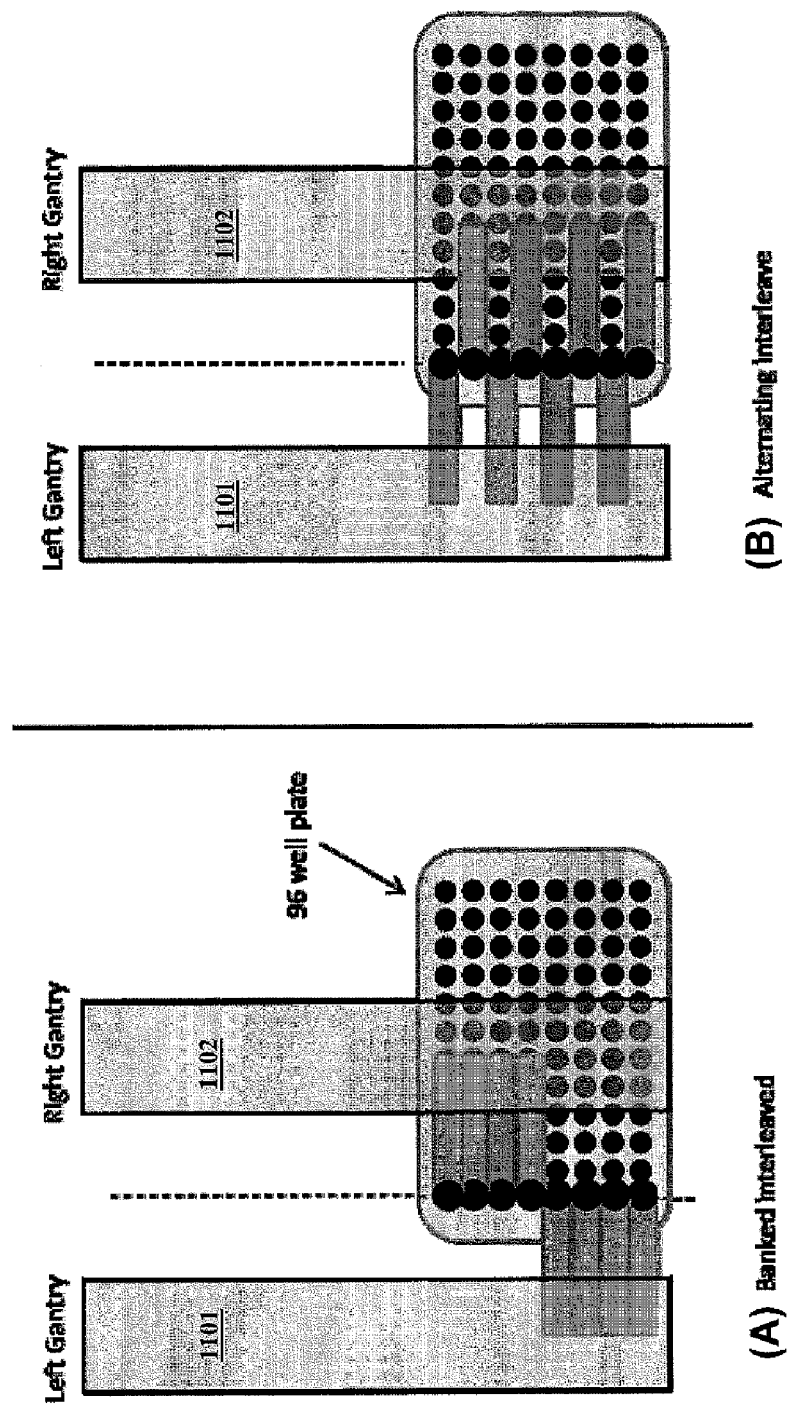
FIG. 11(A) shows a configuration of eight pipettors from two gantries aligned at the same X location for use with a 96-well plate in accordance with one embodiment of the invention.
FIG. 11(B) shows another configuration of eight pipettors from two gantries aligned at the same X location for use with a 96-well plate in accordance with one embodiment of the invention.
Figure 12:
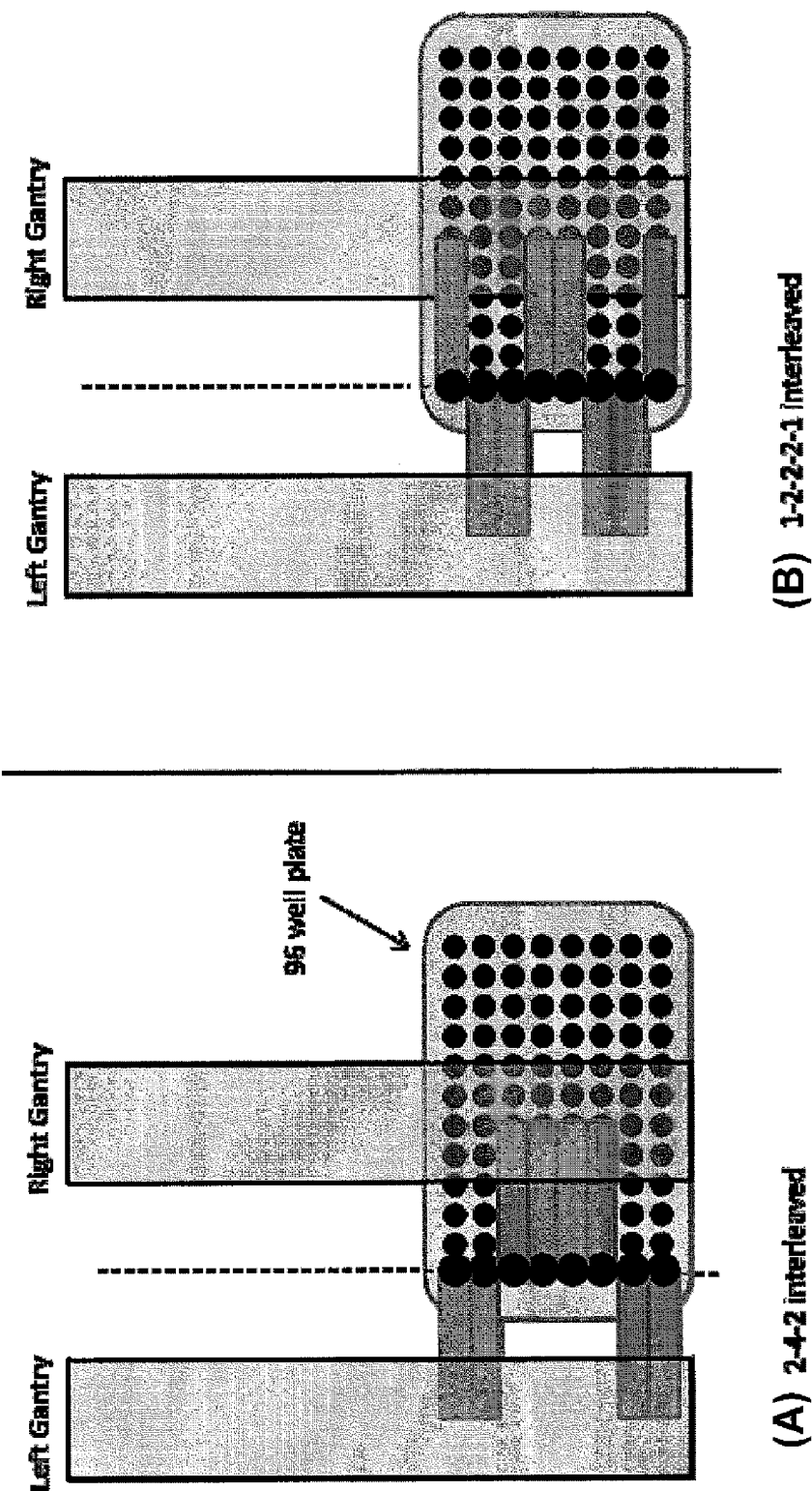
FIG. 12(A) shows another configuration of eight pipettors from two gantries aligned at the same X location for use with a 96-well plate in accordance with one embodiment of the invention.
FIG. 12(B) shows another configuration of eight pipettors from two gantries aligned at the same X location for use with a 96-well plate in accordance with one embodiment of the invention.

Similarly, FIG. 12(A) and FIG. 12(B) illustrate two more alternative configurations of the pipettors. FIG. 12(A) shows a configuration with a 2-4-2 interleave, while FIG. 12(B) shows a 1-2-2-2-1 interleave configuration. The configurations shown in FIGS. 11 and 12 are for illustration only. One skilled in the art would appreciate that other combinations and permutations are possible with such a dual gantry system. For example, while the examples use four pipettors on each gantry, different numbers of pipettors may be included in each gantry. For example, each gantry may have from one to any suitable number of pipettors (e.g., 2, 3, 4, 5, 6, 7, 8, 9, 10, or more pipettors), and the two gantries may have the same or different numbers of pipettors.

The various configurations endow the dual-gantry systems with flexibilities that would not be possible with a single-gantry system. For example, the different configurations can be interchanged any time—e.g., one can change the configuration during a protocol. For example, the configuration in FIG. 11(A) may be used to withdraw liquid samples from the first column of a 96-well plate. Then, the configuration may be changed to that of FIG. 11(B), FIG. 12(A), or FIG. 12(B), before the liquid samples are delivered (either to the same column or a different column in the 96-well plate). Such operations would not be possible (or would be cumbersome and time consuming) with a conventional single-gantry liquid handling system.

One key feature of a dual-gantry system of the invention, as illustrated in FIGS. 7-11, is the fact that system can be interleaved in a variety of manners. The hardware design allows algorithms to take advantage of the capabilities to further increase the throughputs of the system because it is no longer a limitation in the hardware.

How the system needs to interleave (i.e., reconfigure) for the next step may depend on the configuration in the immediate prior step in a transfer protocol. For example, if the last transfer involves a pipettor configuration similar to those in FIG. 9(A) or 9(B) and the next transfer step requires a grid spacing to match a 96 well plate, then the most efficient approach to reconfiguration of the pipettors is to drive the pipettors to a configuration shown in FIG. 11(A).

On the other hand, if the prior configuration is similar to that in FIG. 10(A) or FIG. 10(B) and the next transfer step requires a grid spacing to match a 96 well plate, then the most efficient approach to reconfiguration of the pipettors is to drive the pipettors to a configuration shown in FIG. 11(B).

Figure 13:
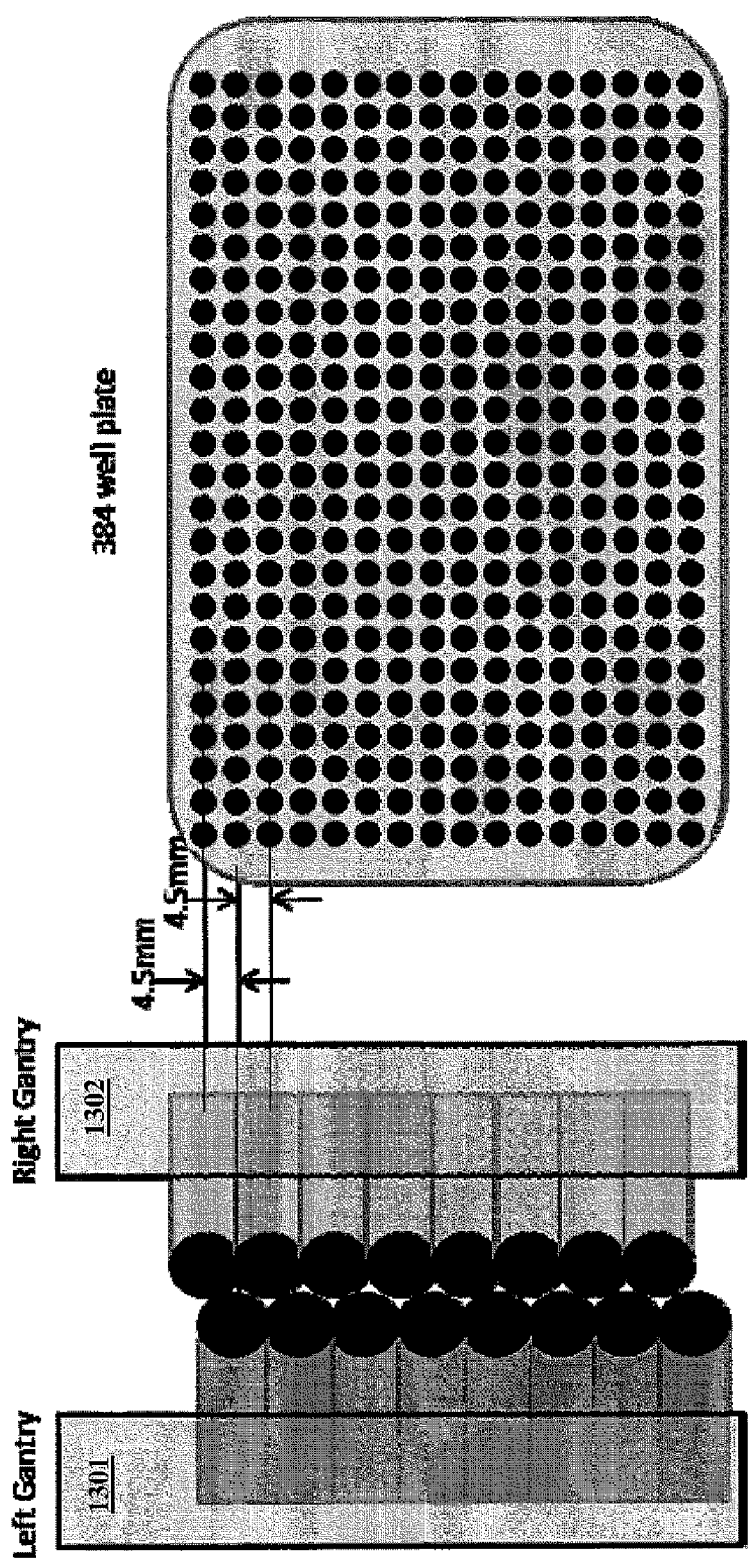
FIG. 13 shows a configuration of 16 pipettors from two gantries aligned interlaced for use with a 384-well plate in accordance with one embodiment of the invention.

The above description illustrates the flexibility of a dual-gantry system that may not be possible using a conventional single-gantry system. FIG. 13 further illustrates another example of functions that is possible with a dual gantry system, but is not possible with a conventional single-gantry system.

As shown in FIG. 13, a liquid handling system includes two gantries 1301 and 1302, each of which includes eight pipettors. To use such a system with a 384-well plate, which has a well pitch of 4.5 mm, the system needs to be able to adopt a configuration with such a spacing between neighboring pipettors. Assuming one has pipettors with a thickness larger than 4.5 mm, it would not be possible to pack a group of pipettors in a single gantry system to achieve such a spacing between the pipettors. However, with a dual gantry system of the invention, one can arrange the two groups of pipettors in an offset manner, as shown in FIG. 13. In this configuration, the pipetting groups can be moved across the columns of the microtiter plate and cover substantially all wells in one run.

FIG. 13 shows a configuration in which the two groups of pipettors are offset (interlaced) by one-half pipettor spacing. Other configurations, such as with one-and-a-half, two-and-a-half, etc. pipettor spacing offsets, are also possible, if needed.

The above examples illustrate how the two gantries in a dual-gantry system can cooperate to perform different tasks, some of which may be difficult or impossible with a single-gantry system. One skilled in the art would appreciate that embodiments of the invention can also be used as a single gantry system, either using one of the two gantries or using both gantries independently as if there were two single-gantry systems.

Furthermore, while the above examples describe two-gantry systems. Embodiments of the invention may also include more than two gantries, such as a three-gantry system, a four gantry system, or even more gantries. For example, a three-gantry system may function like a traditional single-gantry system plus a dual-gantry system of the invention, while a four-gantry system may function like a pair of a dual-gantry system described above.

Figure 14:
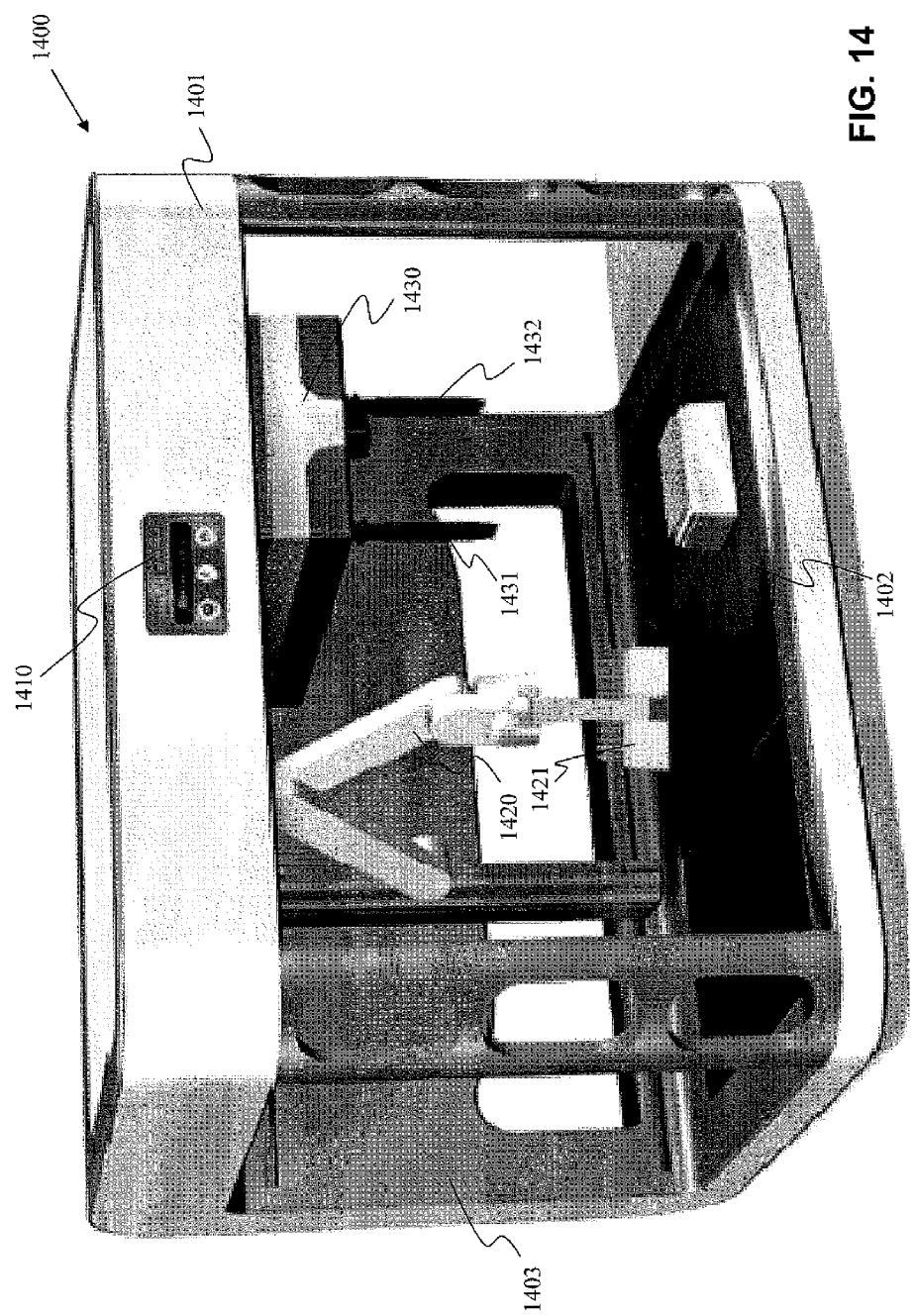
FIG. 14 shows a liquid handling system in accordance with one embodiment of the invention.

In addition, a liquid handling system of the invention may be used with other automation devices. For example, FIG. 14 shows a automated workstation for sample processing. As shown, the workstation 1400 includes a frame or housing, which for example may comprise a floor 1402, a back wall 1403, and a canopy 1404. The floor 1402 includes the work area. The canopy may house motors and electronics, such as a processor and display unit 1401. The processor and display unit 1401 may include memory for storing programs that control the functions of the various parts in the workstation 1400. In some embodiments, the workstation 1400 may be connected to a computer (such as a personal computer), which may provide the memory, programs, display, an input-output devices.

The workstation 1400 may include a robotic arm 1420 in addition to a liquid handling system 1430. The robotic arm 1420 may be used to move labware 1421 (e.g., microtiter plates or tubes) in the work area. The liquid handling system 1430 may have dual pipetting groups 1431 and 1432.

Figure 15:
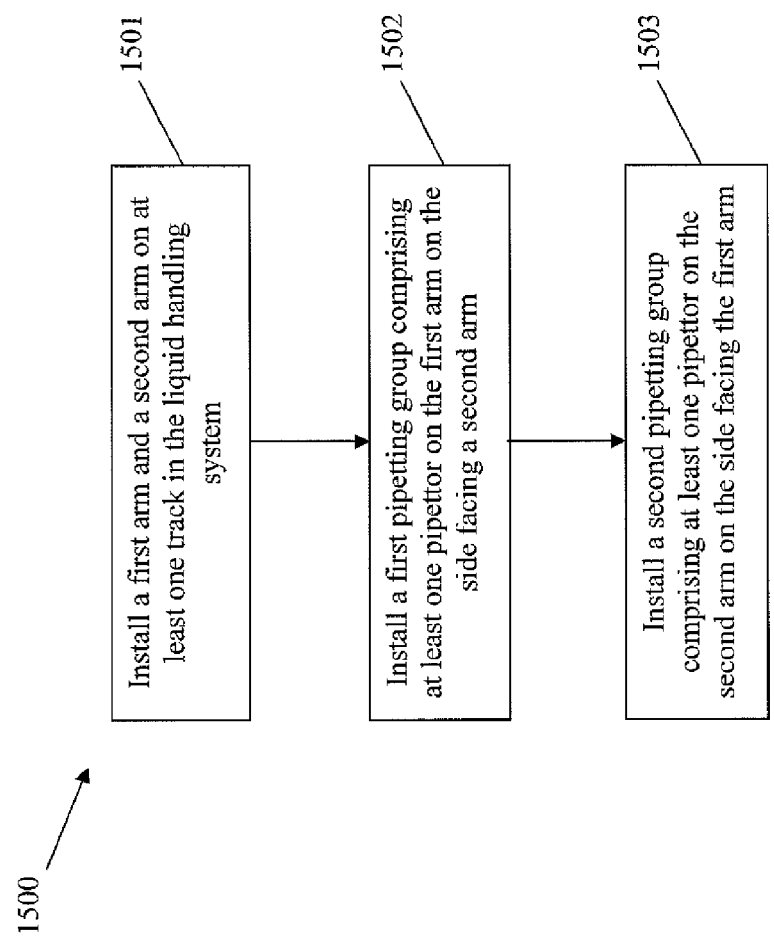
FIG. 15 shows a flow chart illustrating a method for manufacturing a liquid handling system in accordance with one embodiment of the invention.

Some embodiments of the invention relate to methods for manufacturing a liquid handling system of the invention. As shown in FIG. 15, a method 1500 for manufacturing a dual-gantry liquid handling system may include the following steps: First, a first arm (Y spanning assembly) and a second arm are installed on at least one track in the liquid handling system in a manner such that the first arm and the second arm can independently move along the at least one track while maintaining a parallel relationship between the first arm and the second arm (step 1501).

In preferred embodiments, the Y-spanning assembly may be suspended on two tracks (or two rails). The first arm (or Y-spanning assembly) may be suspended on two rails, front and back, and second arm is added (but rotated 180 degrees). Each arm may be driven by a pair (front and rear) of lead screws and nuts. The front and rear nuts may be connected by a common belt and motor such that they will move approximately in tandem.

Although it is possible to suspend the first and second arms on only one rail (e.g., the back rail), this configuration may not provide sufficient rigidity and, therefore, the position accuracy needed for some applications may be difficult to achieve. For example, to accurately address multiple 1536-well plates simultaneously, it would be important for the multiple pipettors on the first and second arms to be highly parallel to the columns in labware in the working area.

Next, a first pipetting group comprising at least one pipettor is installed on the first arm (step 1502), and a second pipetting group comprising at least one pipettor is installed on the second arm (step 1503). In these installations, the at least one pipettor of the first pipetting group is installed on a side of the first arm facing the second pipetting group, and the at least one pipettor of the second pipetting group is installed on a side of the second arm facing the first pipetting group.

Installation of the pipetting group may involve installing pipettor cards on to rails on the first and second arms. To accommodate a spacing of a 96-well plate, the thickness of each pipettor card may be less than 9 mm. The pipettors are installed in the first and second arms in a manner that they can independently move in the Y-axis direction. The movement mechanism may comprise any suitable mechanism. For example, it may include one or more fixed lead screws on the first and second arms, and each pipettor card is driven along one lead screw by a motor which has a lead screw nut imbedded in a rotor.

For determination of the Y-axis locations, an encoder mechanism may be included. For example, each arm may include a linear encoder strip, and each pipettor card may be equipped with a read head. To accommodate the small dimension, the read head may be a small integrated circuit chip mounted to a small custom PCB (printed circuit board).

Embodiments of the invention may include one or more of the following advantages. Embodiments of the invention provide independent, fast, multi-head spanning pipettors with full deck accessibility. Embodiments of the invention can work with labware ranging from single well devices (e.g., tubes, vials) to high density multi-well devices (e.g., 1536 SBS). Embodiments of the invention having dual pipetting groups to allow aspiration and dispense in more locations at the same time. This is particularly advantageous for "random to ordered" pipetting operations. Current liquid handling systems using a single group of pipettors can only operate on one row of liquid reservoirs at once, while a dual-gantry configuration system according to embodiments of the invention can operate in two different positions at the same time. In addition, a dual gantry system can potentially reduce the time to gather samples (aspirate) by half, and then to reduce the time to dispense the sample by half, depending on the particular arrangement of fluid reservoirs and sampling protocol.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention.

What is claimed is:

1. A liquid handling system, comprising:
   a first pipetting group, comprising at least one pipettor, movably arranged on a first arm, wherein each of the at least one pipettor is independently movable in a Y-axis direction, which is parallel with a longitudinal axis of the first arm, and in a Z-axis direction, which is perpendicular to the Y-axis direction; and
   a second pipetting group, comprising at least one pipettor, movably arranged on a second arm, wherein each of the at least one pipettor is independently movable in the Y-axis direction and in a Z-axis direction, wherein the first arm and the second arm are movably arranged on at least one track such that the first arm and the second arm can independently move along the at least one track in a X-axis direction, which is perpendicular to the Y-axis direction and the Z-axis direction, while keeping the first arm parallel with the second arm, wherein the at least one pipettor of the first pipetting group is arranged on a side of the first arm immediately facing the second pipetting group, wherein the at least one pipettor of the second pipetting group is arranged on a side of the second arm immediately facing the first pipetting group.

2. The liquid handling system of claim 1, wherein the first pipetting group comprises four or eight pipettors.

3. The liquid handling system of claim 2, wherein the second pipetting group comprises four or eight pipettors.

4. The liquid handling system of claim 3, wherein a spacing between neighboring pipettors is 9 mm or less.

5. The liquid handling system of claim 1, further comprising a robotic arm.

6. A method for manufacturing a liquid handling system, comprising:
   installing a first arm and a second arm on at least one track in the liquid handling system such that the first arm and the second arm can independently move along the at least one track while keeping the first arm parallel with the second arm;
   installing a first pipetting group, comprising at least one pipettor, on the first arm, wherein each of the at least one pipettor is independently movable in a Y-axis direction, which is parallel with a longitudinal axis of the first arm, and in a Z-axis direction, which is perpendicular to the Y-axis direction; and
   installing a second pipetting group, comprising at least one pipettor, on the second arm, wherein each of the at least one pipettor is independently movable in the Y-axis direction and in a Z-axis direction, wherein the at least one pipettor of the first pipetting group is installed on a side of the first arm immediately facing the second pipetting group, wherein the at least one pipettor of the second pipetting group is installed on a side of the second arm immediately facing the first pipetting group.

7. The method of claim 6, wherein the first pipetting group comprises four or eight pipettors.

8. The method of claim 7, wherein the second pipetting group comprises four or eight pipettors.

9. The method of claim 8, wherein a spacing between neighboring pipettors is 9 mm or less.

10. A liquid handling system, comprising:
a first pipetting group, comprising a first plurality of pipettors, each of the first plurality of pipettors comprising a single barrel and tip, movably arranged on a first arm, wherein each of the first plurality of pipettors is independently movable in a Y-axis direction, which is parallel with a longitudinal axis of the first arm, and in a Z-axis direction, which is perpendicular to the Y-axis direction; and
a second pipetting group, comprising a second first plurality of pipettors, each of the second plurality of pipettors comprising a single barrel and tip, movably arranged on a second arm, wherein each of the first and second pluralities of pipettors is independently movable in the Y-axis direction and in a Z-axis direction, wherein the first arm and the second arm are movably arranged on at least one track such that the first arm and the second arm can independently move along the at least one track in a X-axis direction, which is perpendicular to the Y-axis direction and the Z-axis direction, while keeping the first arm parallel with the second arm, wherein the first plurality of pipettors of the first pipetting group is arranged on a side of the first arm facing the second pipetting group, and the second plurality of pipettors of the second pipetting group is arranged on a side of the second arm immediately facing the first pipetting group.

11. The liquid handling system of claim 10, wherein the first pipetting group comprises four or eight pipettors.

12. The liquid handling system of claim 11, wherein the second pipetting group comprises four or eight pipettors.

13. The liquid handling system of claim 12, wherein a spacing between neighboring pipettors is 9 mm or less.

14. The liquid handling system of claim 10, further comprising a robotic arm.

* * * * *